United States Patent
Tee et al.

(10) Patent No.: US 11,944,870 B2
(45) Date of Patent: Apr. 2, 2024

(54) MOVEMENT DETERMINATION METHOD, MOVEMENT DETERMINATION DEVICE AND COMPUTER-READABLE STORAGE MEDIUM

(71) Applicant: BOMDIC INC., New Taipei (TW)

(72) Inventors: Leong Kian Tee, New Taipei (TW); Haoyi Chih, New Taipei (TW); En-Tzu Wang, New Taipei (TW)

(73) Assignee: BOMDIC INC., New Taipei (TW)

( * ) Notice: Subject to any disclaimer, the term of this patent is extended or adjusted under 35 U.S.C. 154(b) by 78 days.

(21) Appl. No.: 17/709,426

(22) Filed: Mar. 31, 2022

(65) Prior Publication Data
US 2023/0310934 A1 Oct. 5, 2023

(51) Int. Cl.
*A63B 24/00* (2006.01)

(52) U.S. Cl.
CPC ...... *A63B 24/0062* (2013.01); *A63B 24/0006* (2013.01); *A63B 2024/0012* (2013.01); *A63B 2024/0068* (2013.01); *A63B 2024/0071* (2013.01); *A63B 2220/806* (2013.01); *A63B 2230/62* (2013.01)

(58) Field of Classification Search
None
See application file for complete search history.

(56) References Cited

U.S. PATENT DOCUMENTS

| | | | |
|---|---|---|---|
| 2017/0368413 A1* | 12/2017 | Shavit | A63B 24/0075 |
| 2018/0239430 A1* | 8/2018 | Tadi | G06F 3/015 |
| 2019/0091515 A1* | 3/2019 | Shavit | A63B 24/0006 |
| 2021/0338110 A1* | 11/2021 | Gingrich | A61B 5/7264 |
| 2021/0346761 A1* | 11/2021 | Sterling | G06V 20/46 |
| 2022/0023730 A1* | 1/2022 | Howenstein | A63B 69/3685 |
| 2022/0126190 A1* | 4/2022 | Kim | G06V 10/34 |
| 2022/0161117 A1* | 5/2022 | Jessop | G16H 50/30 |
| 2022/0362630 A1* | 11/2022 | Lee | G06T 7/70 |
| 2023/0025516 A1* | 1/2023 | Wang | G10L 15/22 |
| 2023/0082953 A1* | 3/2023 | Berger | G06V 20/44 |

* cited by examiner

*Primary Examiner* — Reginald A Renwick
(74) *Attorney, Agent, or Firm* — JCIPRNET (57) ABSTRACT

The disclosure provides a movement determination method, a movement determination device, and a computer-readable storage medium. The method includes the following. In response to determining that a user has presented an initial movement corresponding to a to-be-detected movement, an anchor joint point among multiple joint points of the user is decided based on the to-be-detected movement. A movable range of each of the anchor joint points is decided. In response to determining that each of the anchor joint points leaves the corresponding movable range, it is determined that the user has stopped performing the to-be-detected movement.

19 Claims, 7 Drawing Sheets

MOVEMENT DETERMINATION METHOD, MOVEMENT DETERMINATION DEVICE AND COMPUTER-READABLE STORAGE MEDIUM

BACKGROUND

Technical Field

The disclosure relates to a motion detection mechanism, and more particularly, to a movement determination method, a movement determination device, and a computer-readable storage medium.

Description of Related Art

In modern society, the technology of detecting a user's motion through special equipment is quite common. For example, in conventional technology, technical means have been proposed to obtain corresponding motion data by analyzing the images after obtaining images of the user during the motion process. However, in addition to obtaining the images of the user during the motion process, these techniques usually require special equipment and/or a complex image acquisition device.

Therefore, if a simple image acquisition device may be used to detect whether the user completes a set of exercise motions correctly through image analysis technology, it should be helpful to obtain relevant motion data, improve the user's exercise motions, and enhance the convenience of exercise for the user, so as to develop a fixed exercise habit.

SUMMARY

In view of the above, the disclosure provides a movement determination method, a movement determination device, and a computer-readable storage medium, which may be used to solve the above technical issues.

The disclosure provides a movement determination method, suitable for a movement determination device, including the following. In response to determining that a user has presented an initial movement corresponding to a to-be-detected movement, at least one anchor joint point among multiple joint points of the user is decided based on the to-be-detected movement. A movable range of each of the anchor joint points is decided. In response to determining that each of the anchor joint points leaves the corresponding movable range, it is determined that the user has stopped performing the to-be-detected movement.

The disclosure provides a movement determination device, including a storage circuit and a processor. The storage circuit stores a program code. The processor is coupled to the storage circuit and accesses the program code to perform the following. In response to determining that a user has presented an initial movement corresponding to a to-be-detected movement, at least one anchor joint point among multiple joint points of the user is decided based on the to-be-detected movement. A movable range of each of the anchor joint points is decided. In response to determining that each of the anchor joint points leaves the corresponding movable range, it is determined that the user has stopped performing the to-be-detected movement.

The disclosure provides a computer-readable storage medium. The computer-readable storage medium records an executable computer program, and the executable computer program is loaded by a movement determination device to perform the following. In response to determining that a user has presented an initial movement corresponding to a to-be-detected movement, at least one anchor joint point among multiple joint points of the user is decided based on the to-be-detected movement. A movable range of each of the anchor joint points is decided. In response to determining that each of the anchor joint points leaves the corresponding movable range, it is determined that the user has stopped performing the to-be-detected movement.

DETAILED DESCRIPTION OF DISCLOSED EMBODIMENTS

Figure 1:
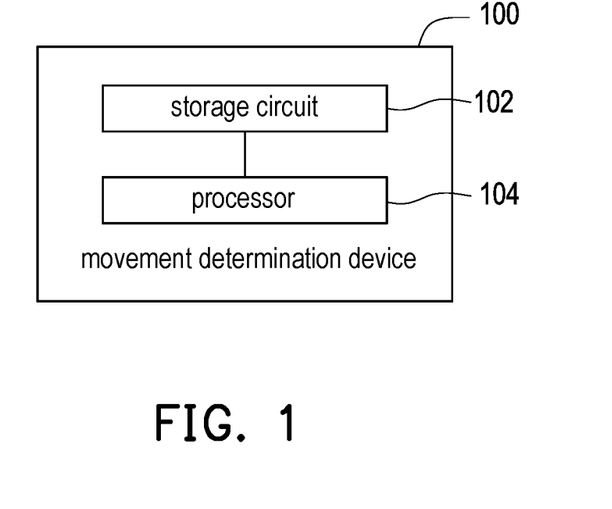
FIG. 1 is a schematic view of a movement determination device according to an embodiment of the disclosure.

Referring to FIG. 1, FIG. 1 is a schematic view of a movement determination device according to an embodiment of the disclosure. In different embodiments, a movement determination device 100 may be implemented as various electronic devices/intelligent devices/computer devices. In some embodiments, the movement determination device 100 may obtain one or more videos/images of the image capturing devices/elements when a user performs a certain to-be-detected movement (e.g., push-ups, sit-ups, squats, or pull-ups) from other image capturing devices/elements, and then perform movement determination on the user accordingly.

In other embodiments, the movement determination device 100 may also have the above image capturing devices/elements built in, and then may perform the movement determination on the user after capturing the one or more videos/images of the movement of the user.

In FIG. 1, the movement determination device 100 includes a storage circuit 102 and a processor 104. The storage circuit 102 is, for example, any type of fixed or removable random access memory (RAM), read-only memory (ROM), flash memory, hard disk, other similar devices, or a combination of these devices, and may be configured to record multiple program codes or modules.

The processor 104 is coupled to the storage circuit 102, and may be a general-purpose processor, a special-purpose processor, a conventional processor, a digital signal processor, multiple microprocessors, one or more microprocessors combined with a digital signal processor core, a controller, a microcontroller, an application specific integrated circuit (ASIC), a field programmable gate array (FPGA), any other kind of integrated circuits, a state machine, an advanced RISC machine (ARM) processor, and the like.

In an embodiment of the disclosure, the processor 104 may access the modules and the program codes recorded in the storage circuit 102 to implement a movement determination method provided by the disclosure, and details thereof are described below.

Figure 2:
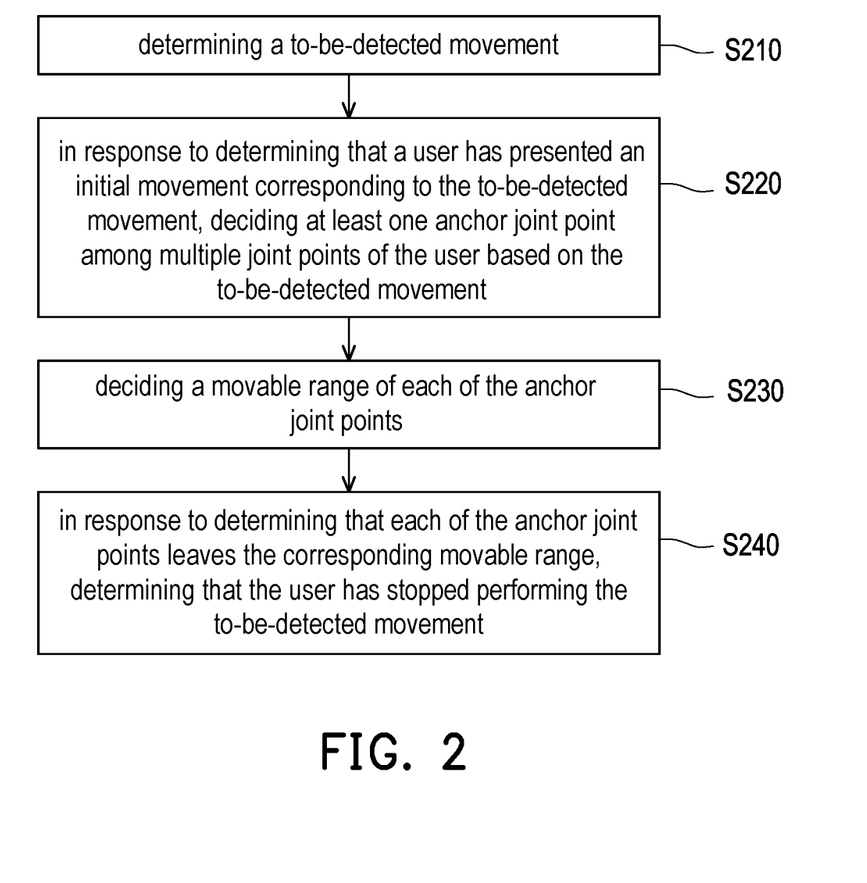
FIG. 2 is a flowchart of a movement determination method according to an embodiment of the disclosure.

Referring to FIG. 2, FIG. 2 is a flowchart of a movement determination method according to an embodiment of the disclosure. The method in this embodiment may be performed by the movement determination device 100 in FIG. 1, and details of each of the steps in FIG. 2 will be described below with the elements shown in FIG. 1.

In step S210, the processor 104 determines the to-be-detected movement. In an embodiment, the to-be-detected movement is, for example, an exercise movement to be performed by the user. In an embodiment, the processor 104 may provide a user interface, and may provide various exercise movements that may be detected by the movement determination device 100 in the user interface.

For ease of description, hereinafter, it is assumed that the movement determination device 100 in the embodiment of the disclosure has a capacity to detect movements such as push-ups, sit-ups, squats, or pull-ups, but the disclosure is not limited thereto. In this case, the processor 104 may, for example, display options corresponding to the above movements in the user interface for the user to reference or select. After that, the processor 104 may use the movement selected by the user as the to-be-detected movement.

In another embodiment, the processor 104 may automatically determine the to-be-detected movement based on the images of the user captured by the image capturing devices/elements. In an embodiment, after obtaining the images of the user, the processor 104 may, for example, feed the images of the user into a pre-trained movement recognition model, so that the movement recognition model recognizes what movement the user is performing based on the images of the user, and then use a recognition result of the movement recognition model as the to-be-detected movement.

In different embodiments, the movement recognition model may be implemented as various machine learning models and neural networks, but the disclosure is not limited thereto. In order to enable the movement recognition model to have the above capabilities, the processor 104 may pre-train the movement recognition model based on specific training data. For example, after obtaining an image of a person performing a certain movement A (e.g., the push-up), the processor 104 may use the image as a piece of training data, and mark the training data as corresponding to the movement A (e.g., the push-up). Next, the processor 104 may feed the training data into the movement recognition model, so that the movement recognition model may learn relevant image features related to the movement A. Similarly, after obtaining an image of the person performing a certain movement B (e.g., the sit-up), the processor 104 may use the image as a piece of training data, and mark the training data as corresponding to the movement B (e.g., the sit-up). Next, the processor 104 may feed the training data into the movement recognition model, so that the movement recognition model may learn relevant image features related to the movement B.

After the above training, when the movement recognition model receives the image of the certain movement, the movement recognition model may accordingly recognize what kind of movement the person in the image of the movement should be performing, but the disclosure is not limited thereto.

In an embodiment, the processor 104 may determine whether the user has presented an initial movement corresponding to the to-be-detected movement. For example, assuming that the considered to-be-detected movement is the push-up, the processor 104 may determine whether the user presents an initial movement of the push-up based on the obtained images of the user. For another example, assuming that the considered to-be-detected movement is the squat, the processor 104 may determine whether the user presents an initial movement of the squat based on the obtained images of the user. In another embodiment, since different to-be-detected movements correspond to different specific initial movements, the processor 104 may automatically determine the to-be-detected movement to be performed by the user by recognizing the specific initial movement after obtaining the images of the user.

In step S220, in response to determining that the user has presented the initial movement corresponding to the to-be-detected movement, the processor 104 decides at least one anchor joint point among multiple joint points of the user based on the to-be-detected movement.

In the embodiment of the disclosure, the processor 104 may detect each of joint points on the user in each of the images of the user based on a relevant detection algorithm of human joint points (e.g., DeepPose), such as shoulder joint points, wrist joint points, ankle joint points, hip joint points, finger joint points, nose joint points, elbow joint points, knee joint points. However, the disclosure is not limited thereto.

In an embodiment, in response to determining that the to-be-detected movement is the push-up or the pull-up, the processor 104 detects the wrist joint points of the user as the anchor joint points. In an embodiment, in response to determining that the to-be-detected movement is the squat, the processor 104 detects the ankle joint points of the user as the anchor joint points. In response to determining that the to-be-detected movement is the sit-up, the processor 104 detects the hip joint points of user as the anchor joint points.

Roughly speaking, the anchor joint point may be understood as a joint point whose position will remain substantially unchanged when the user performs the to-be-detected movement. For example, when the user performs the push-up, palms of the user are generally pressed against a ground, so that positions of the wrist joint points are fixed at a position close to the ground. Therefore, if the to-be-detected movement is the push-up, the processor 104 may select the wrist joint points of the user as the anchor joint points.

For another example, when the user performs the squat, soles of feet of the user are generally pressed against the ground, so that positions of the ankle joint points are fixed at the position close to the ground. Therefore, if the to-be-detected movement is the squat, the processor 104 may select the ankle joint points of the user as the anchor joint points. In addition, when the user performs the sit-up, a buttock of the user is generally pressed against the ground, so that positions of the hip joint points are fixed at the position close to the ground. Therefore, if the to-be-detected movement is the sit-up, the processor 104 may select the hip joint points of the user as the anchor joint points. Furthermore, when the user performs the pull-up, hands of the user generally grip a horizontal bar tightly, so that positions of the wrist joint points are fixed at a position close to the horizontal bar. Therefore, if the to-be-detected movement is the pull-up, the processor 104 may select the wrist joint points of the user as the anchor joint points.

In step S230, the processor 104 decides a movable range of each of the anchor joint points. In an embodiment, the processor 104 may decide a designated length R1, and then decide a geometric region as the movable range of each of the anchor joint points based on each of the anchor joint points and the designated length R1. In an embodiment, each of the movable ranges is, for example, a circular region with the corresponding anchor joint point as a center of circle and the designated length R1 as a radius, but the disclosure is not limited thereto.

In different embodiments, a manner in which the designated length R1 is decided may vary depending on the considered anchor joint points. For example, in response to determining that the anchor joint points are the wrist joint points of the user, the processor 104 may obtain the finger joint points of the user, and decide the designated length R1 based on a first distance between the wrist joint points and the corresponding finger joint points. For example, the processor 104 may set the designated length R1 to be a result of multiplying the first distance by a certain scale value (e.g., 1 to 2 times), but the disclosure is not limited thereto.

In an embodiment, in response to determining that the anchor joint points are the ankle joint points of the user, the processor 104 may obtain toe joint points of the user, and decide the designated length R1 based on a second distance between the ankle joint points and the corresponding toe joint points. For example, the processor 104 may set the designated length R1 to be a result of multiplying the second distance by the certain scale value (e.g., 1 to 2 times), but the disclosure is not limited thereto.

In another embodiment, in response to determining that the anchor joint points are the hip joint points of the user, the processor 104 may obtain the knee joint points of the user, and decide the designated length R1 based on a third distance between the hip joint points and the corresponding knee joint points. For example, the processor 104 may set the designated length R1 to be a result of multiplying the third distance by the certain scale value (e.g., 0.5 to 1 times), but the disclosure is not limited thereto.

In other embodiments, the processor 104 may also implement the movable range in other forms. Each of the movable ranges is, for example, a square region with the corresponding anchor joint point as a center and the designated length R1 as a side length, but the disclosure is not limited thereto.

In an embodiment, the processor 104 may determine whether each of the anchor joint points leaves the corresponding movable range. In the embodiment of the disclosure, the movable range may be roughly understood as a range that the anchor joint point may be allowed to move when the user performs the to-be-detected movement without determining that the user has completed the to-be-detected movement.

As mentioned earlier, when the user performs the to-be-detected movement, a position of the anchor joint point should be substantially fixed. In this case, if the processor 104 determines that each of the anchor joint points has not left the corresponding movable range, it means that the user is still performing the to-be-detected movement. Based on this, the processor 104 may determine that the user has not stopped performing the to-be-detected movement.

On the other hand, if the processor 104 determines that each of the anchor joint points has left the corresponding movable range, it means that the user has left the initial movement of the to-be-detected movement. That is, it means that the user has stopped performing the to-be-detected movement. Based on this, in step S240, in response to determining that each of the anchor joint points leaves the corresponding movable range, the processor 104 determines that the user has stopped performing the to-be-detected movement.

In order for the disclosure to be more comprehensible, several embodiments are further described below.

Figure 3:
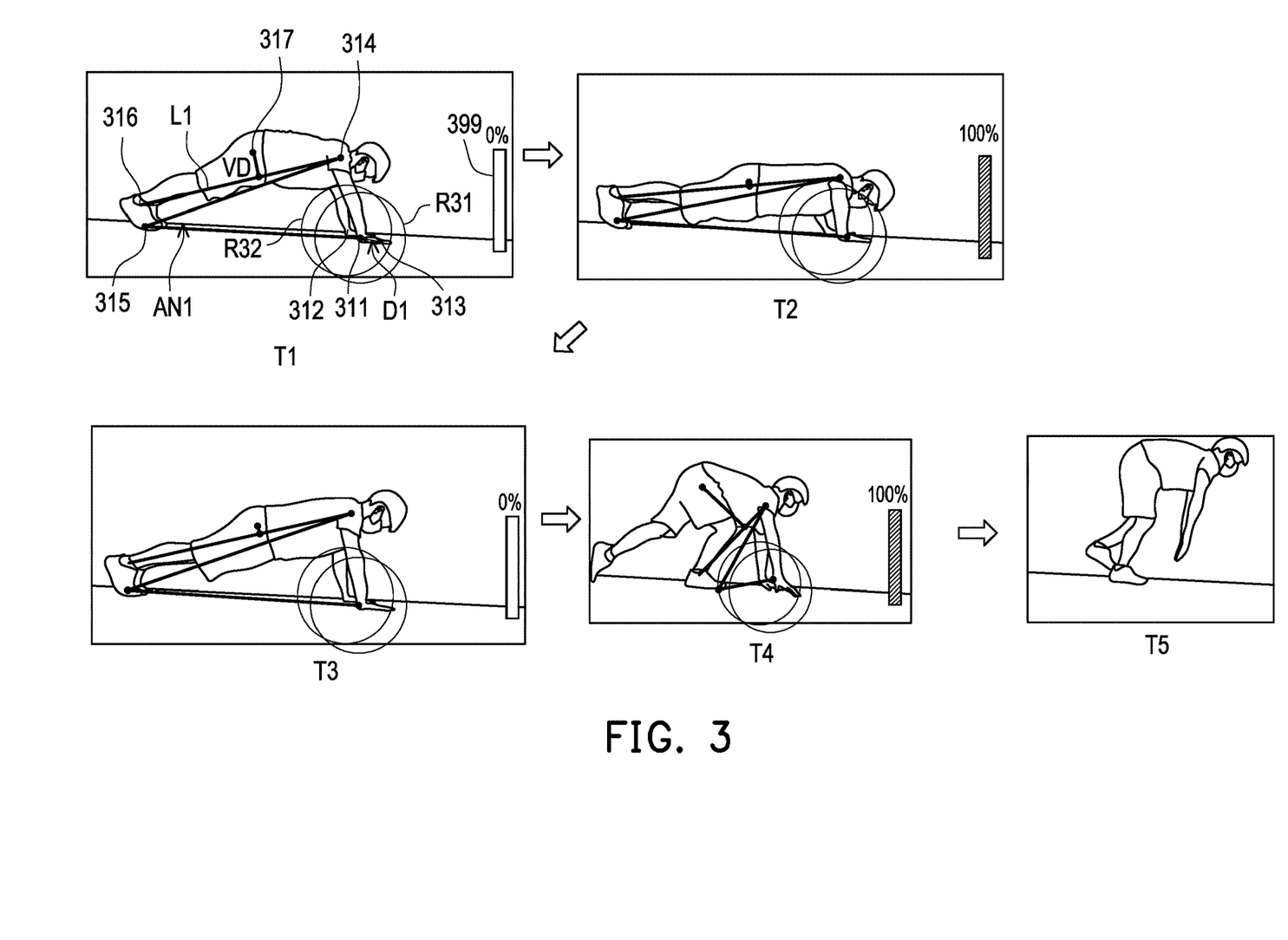
FIG. 3 is a schematic view of an application scenario according to the first embodiment of the disclosure.

Referring to FIG. 3, FIG. 3 is a schematic view of an application scenario according to the first embodiment of the disclosure. In FIG. 3, five images of the user shown respectively correspond to time points T1 to T5, for example. In the first embodiment, it is assumed that the to-be-detected movement determined in step S210 is the push-up. Afterwards, the processor 104 may determine whether the user has presented the initial movement of the push-up.

At the time point T1, since a posture of the user has been presented as the initial movement of the push-up, the processor 104 may accordingly decide the anchor joint point among the joint points of the user.

In the first embodiment, since the considered to-be-detected movement is the push-up, the processor 104 may determine that wrist joint points 311 and 312 (respectively corresponding to a right wrist and a left wrist of the user) of the user are the anchor joint points, and decides the movable ranges of the anchor joint points.

In FIG. 3, the processor 104 may obtain a finger joint point 313 of the user, and decide the designated length R1 based on a first distance D1 between the wrist joint point 311 and the corresponding finger joint point 313. The processor 104 may directly use a length twice as long as the first distance D1 as the designated length R1, and define movable ranges R31 and R32 accordingly. The movable range R31 is, for example, a circular range with the wrist joint point 311 as the center of circle and the designated length R1 as the radius, while the movable range R32 is, for example, a circular range with the wrist joint point 312 as the center of circle and the designated length R1 as the radius. However, the disclosure is not limited thereto. After the movable ranges R31 and R32 are decided, positions of the movable ranges R31 and R32 in the image are fixed.

Afterwards, the processor 104 may determine whether the wrist joint points 311 and 312 leave the corresponding movable ranges R31 and R32. If so, it means that the user has stopped performing the push-up (e.g., a state at the time point T5). If not, it means that the user is still in a process of performing the push-up.

In some embodiments, the processor 104 may further recognize the number of times the user performs the to-be-detected movement based on the images of the user in a process of performing the to-be-detected movement, which will be further described below with reference to FIG. 4.

Figure 4:
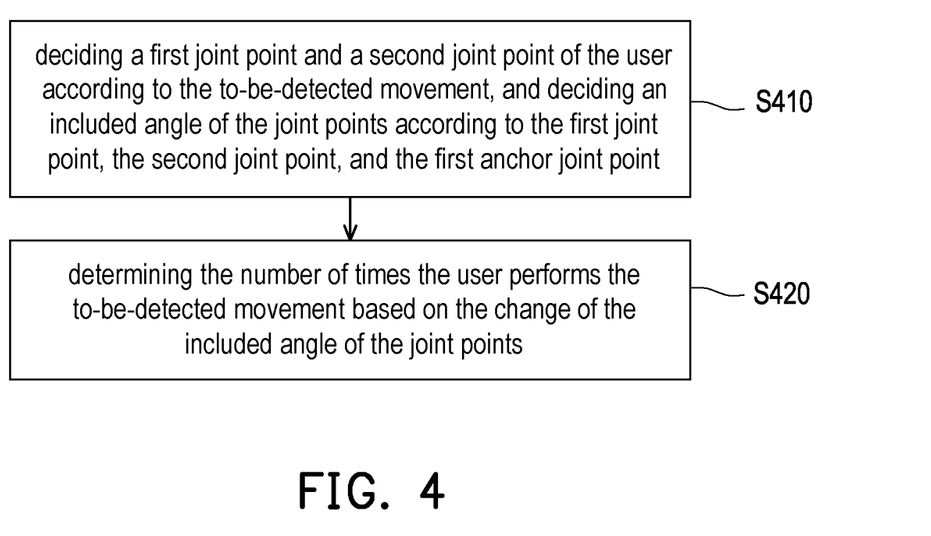
FIG. 4 is a flowchart of recognizing the number of times of movements according to an embodiment of the disclosure.

Referring to FIG. 4, FIG. 4 is a flowchart of recognizing the number of times of movements according to an embodiment of the disclosure. For ease of description, the scenario shown in FIG. 3 is taken as an example for description below. In step S410, the processor 104 may decide a first joint point and a second joint point of the user according to the to-be-detected movement, and decide an included angle AN of the joint points according to the first joint point, the second joint point, and a first anchor joint point. The included angle of the joint points changes in response to the user performing the to-be-detected movement.

In the first embodiment, the first anchor joint point is, for example, the wrist joint point 311, but the disclosure is not limited thereto. In addition, in response to determining that the to-be-detected movement is the push-up, the processor 104 may use a shoulder joint point 314 and a toe joint point 315 of the user as the first joint point and the second joint point respectively, and use an included angle AN1 corresponding to the second joint point as the included angle AN of the joint points.

Next, in step S420, the processor 104 may determine the number of times the user performs the to-be-detected movement based on a change of the included angle AN of the joint points (e.g., the included angle AN1).

In the first embodiment, the processor 104 may decide a current angle change amount (denoted by flexAngle) based on a current angle value (denoted by currentAngle) and an initial angle value (denoted by initialAngle) of the included angle AN of the joint points (e.g., the included angle AN1). In the embodiment of the disclosure, the initial angle value is an initial value of the included angle AN of the joint points, and a value thereof is, for example, a fixed value. In addition, the current angle value is an angle value of the included angle AN of the joint points measured as the user performs the to-be-detected movement. In an embodiment, the current angle change amount is, for example, an absolute difference between the current angle value and the initial angle value, that is, flexAngle=abs(currentAngle−initialAngle), where abs(·) is an absolute value operator.

Next, the processor 104 may decide a reference value RV1 based on the current angle change amount of the included angle AN of the joint points, an angle upper limit value of the joint point (denoted by flexAngleUpper), and an angle lower limit value of the joint point (denoted by flexAngleLower). In an embodiment, the angle upper limit value of the joint point and the angle lower limit value of the joint point are, for example, a maximum value and a minimum value of the included angle AN of the joint points respectively, but the disclosure is not limited thereto. In an embodiment, the reference value RV1 may be represented by:

$$RV1 = \frac{\text{flexAngle} - \text{flexAngleLower}}{(\text{flexAngleUpper} - \text{flexAngleLower}) \times 100}$$

Afterwards, the processor 104 may determine whether a change of the reference value RV1 meets a preset condition. For example, the processor 104 may determine whether the reference value RV1 has changed from a lower limit value to an upper limit value, and then from the upper limit value back to the lower limit value. If so, the processor 104 may determine that the reference value RV1 has met the above preset condition, and determine that the user has performed to-be-detected movement once. Afterwards, the processor 104 may, for example, accumulate the number of times the user performs the current set of to-be-detected movements.

In the above example, the upper limit value and the lower limit value of the reference value RV1 are, for example, 100% and 0%, respectively. In this case, the processor 104 may determine whether the reference value RV1 has increased from 0% to 100%. If so, it means that the user has completed a complete stroke of the push-up. Therefore, the processor 104 may determine that the reference value RV1 has met the preset condition.

Taking FIG. 3 as an example, the processor 104 may present a value of the reference value RV1 in the images of the user in a form of a percentage bar 399 for reference. Therefore, when the processor 104 determines that the user changes from a posture at the time point T1 (corresponding to a state where the reference value RV1 is 0%) to a posture at the time point T2 (corresponding to a state where the reference value RV1 is 100%) in FIG. 3, and then changes from the posture at the time point T2 to a posture at the time point T3 (corresponding to the state where the reference value RV1 is 0%), the processor 104 may determine that the reference value RV1 has met the above preset condition, and determine that the user has performed the push-up once.

On the other hand, if the reference value RV1 does not increase from 0% to 100%, or does not decrease from 100% to 0%, it means that the user has not completed one complete stroke of the push-up. Therefore, the processor 104 may determine that the reference value RV1 does not meet the above preset condition, and thus the number of times the user performs the current set may not be accumulated. In other embodiments, the value of the reference value RV1 may also be presented in a manner other than the percentage. In other embodiments, a number range may be set as a buffer value for the preset condition of the reference value RV1. In other embodiments, the preset condition of the reference value RV1 may also have different values according to difficulty levels.

Taking FIG. 3 as an example again, when the processor 104 determines that the user has changed from the posture at the time point T3 to a posture at the time point T4 in FIG. 3, the processor 104 may, for example, determine that the reference value RV1 has changed from 0% to 100%. However, since the user gets up at the time point T4, the reference value RV1 does not drop from 100% back to 0%. In this case, the processor 104 may determine that the reference value RV1 does not meet the above preset condition, and further determine that the user has not completed the push-up this time.

After the user changes from the posture at the time point T4 to a posture at the time point 15, since the wrist joint points 311 and 312 have left the corresponding movable ranges R31 and R32, the processor 104 may determine that the user has stopped performing the current set of push-ups.

In an embodiment, if the user returns to the posture at the time point T1, it may be determined to perform the next set of push-ups, and the number of times is recalculated as the number of times of the second set.

In view of the above, in the embodiment of the disclosure, in addition to determining whether the user has stopped performing the to-be-detected movement based on a relative position of the anchor joint point and the movable range, it may also determine the number of times the user performs the current to-be-detected movements based on the change of the considered included angle of the joint points.

In some embodiments, the processor 104 may further recognize correctness of the user performing the to-be-detected movement based on the images of the user in the process of performing the to-be-detected movement, which will be further described below with reference to FIG. 5.

Figure 5:
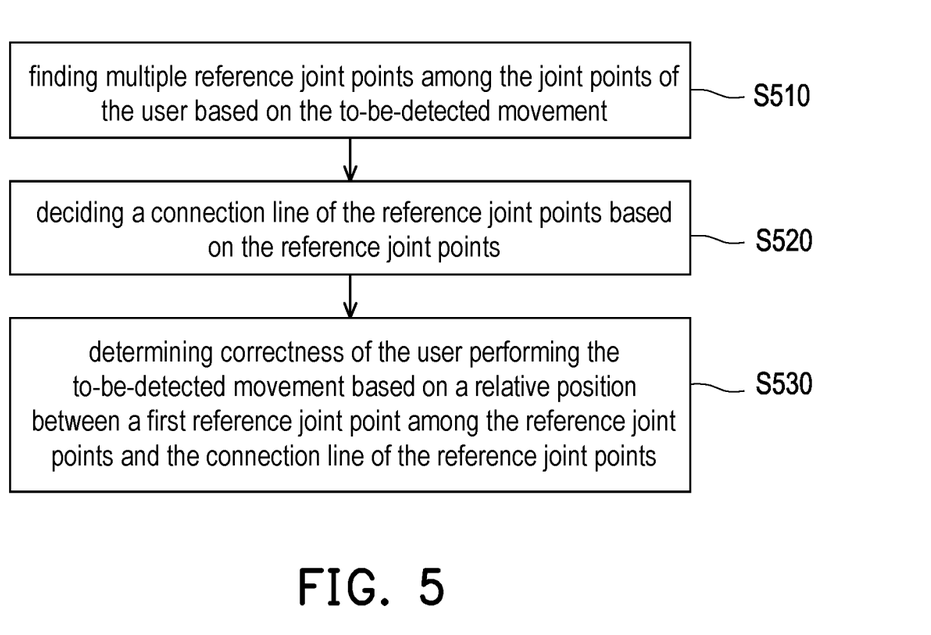
FIG. 5 is a flowchart of recognizing correctness of a movement according to an embodiment of the disclosure.

Referring to FIG. 5, FIG. 5 is a flowchart of recognizing correctness of a movement according to an embodiment of the disclosure. For ease of description, the scenario shown in FIG. 3 is taken as an example for description below. In step S510, the processor 104 may find multiple reference joint points among the joint points of the user based on the to-be-detected movement. In step S520, the processor 104 may decide a connection line LN of the reference joint points based on the reference joint points.

In the first embodiment, the processor 104 may respectively use the shoulder joint point 314, an ankle joint point 316, and a hip joint point 317 of the user as the reference joint points, and use a first connection line L1 between the shoulder joint point 314 and the ankle joint point 316 as the connection line LN of the reference joint points.

Next, in step S530, the processor 104 may determine the correctness of the user performing the to-be-detected movement based on a relative position between a first reference joint point RJ1 among the reference joint points and the connection line LN of the reference joint points.

In the scenario of FIG. 3, the processor 104 may use the hip joint point 317 of the user as the first reference joint point RJ1. Then, the processor 104 may obtain a current vertical distance VD between the first reference joint point RJ1 and the connection line LN of the reference joint points. Afterwards, the processor 104 may estimate the correctness of the user performing the to-be-detected movement based on the current vertical distance VD and a length of the connection line LN of the reference joint points.

In some embodiments, the correctness of the user performing the to-be-detected movement is represented by a ratio of the current vertical distance VD to the length of the connection line LN of the reference joint points. Taking FIG. 3 as an example, if a ratio value is smaller (e.g., a state at the time point T2), it means that the buttock of the user is not raised, and a body is in a straight line, which means that the user performs the push-up more correctly. If the ratio value is greater (e.g., a state at the time point T1), it means that that the way the user performs the push-up is less correct. In other embodiments, the correctness of the to-be-detected movement may also be determined according to the vertical distance VD alone or according to a ratio of the vertical distance VD to other lengths (e.g., a height of the user).

In view of the above, in the embodiment of the disclosure, the correctness of the user performing the to-be-detected movement may be determined through image recognition, thereby improving variety, accuracy, and effectiveness of motion detection.

In the embodiment of the disclosure, although the scenario of push-up shown in FIG. 3 is used as an example for illustration above, the method in the disclosure may also be applied to other to-be-detected movements, which will be further described below.

Figure 6:
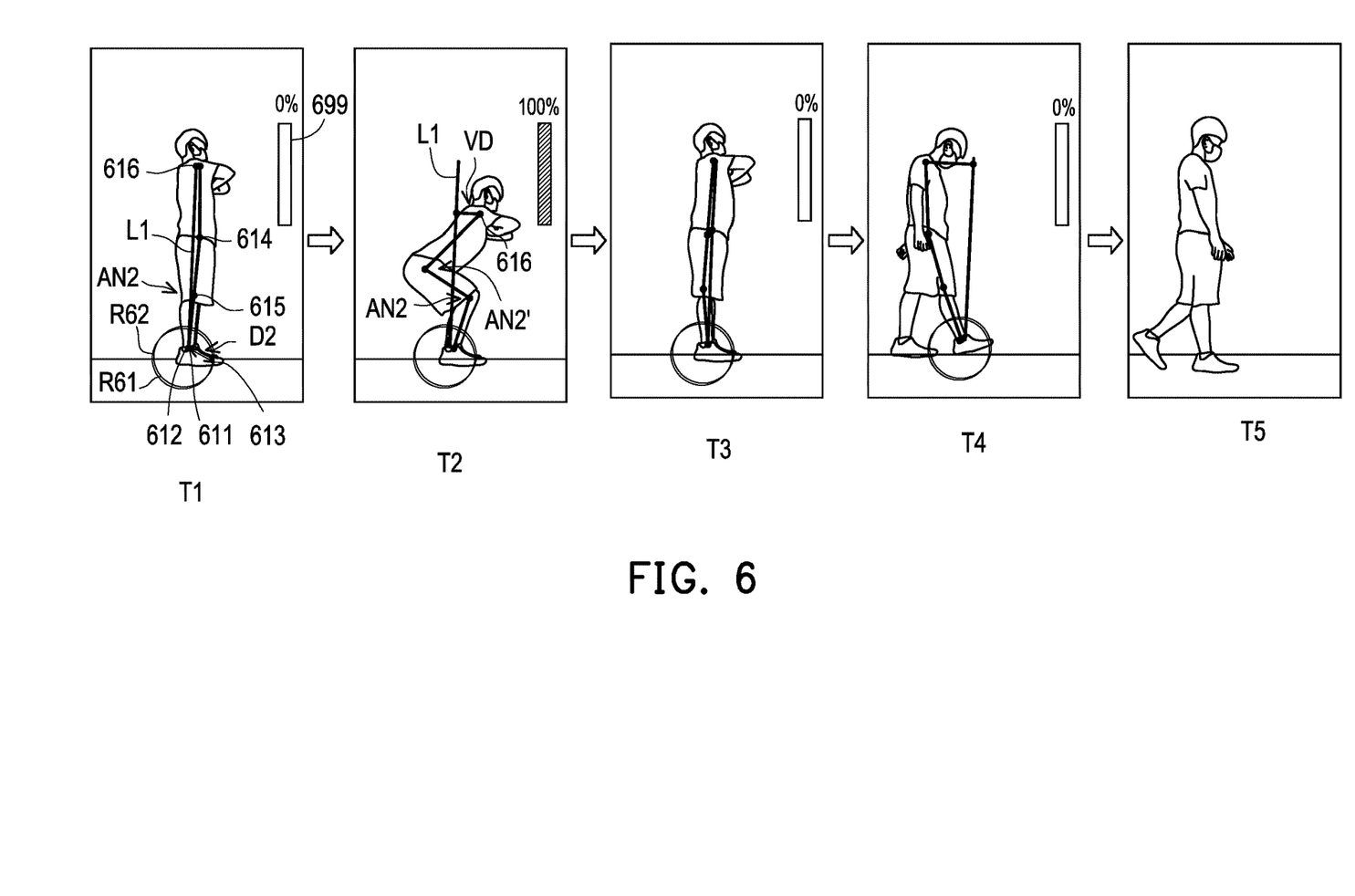
FIG. 6 is a schematic view of an application scenario according to the second embodiment of the disclosure.

Referring to FIG. 6, FIG. 6 is a schematic view of an application scenario according to the second embodiment of the disclosure. In FIG. 6, five images of the user shown respectively correspond to the time points T1 to T5, for example. In the second embodiment, it is assumed that the to-be-detected movement determined in step S210 is the squat. Afterwards, the processor 104 may determine whether the user has presented the initial movement of the squat.

At the time point T1, since the posture of the user has been presented as the initial movement of the squat (e.g., a stand-up posture), the processor 104 may accordingly decide the anchor joint point among the joint points of the user.

In the second embodiment, since the considered to-be-detected movement is the squat, the processor 104 may determine that ankle joint points 611 and 612 (respectively corresponding to a right ankle and a left ankle of the user) of the user are the anchor joint points, and decide the movable ranges of the anchor joint points. In FIG. 6, the processor 104 may obtain a toe joint point 613 of the user, and determine the designated length R1 based on a second distance D2 between the ankle joint point 611 and the corresponding toe joint point 613. The processor 104 may directly use the second distance D2 as the designated length R1, and define movable ranges R61 and R62 accordingly. The movable range R61 is, for example, a circular range with the ankle joint point 611 as the center of circle and the designated length R1 as the radius, while the movable range R62 is, for example, a circular range with the ankle joint point 612 as the center of circle and the designated length R1 as the radius. However, the disclosure is not limited thereto. After the movable ranges R61 and R62 are decided, positions of the movable ranges R61 and R62 in the image are fixed. Afterwards, the processor 104 may determine whether the ankle joint points 611 and 612 leave the corresponding movable ranges R61 and R62. If so, it means that the user has stopped performing the squat (e.g., the state at the time point T5). If not, it means that the user is still in a process of performing the squat.

In some embodiments, the processor 104 may also recognize the number of times the user performs the to-be-detected movement based on the mechanism shown in FIG. 4, which will be further described below.

In step S410, the processor 104 may decide the first joint point and the second joint point of the user according to the to-be-detected movement, and decide the included angle AN of the joint points according to the first joint point, the second joint point, and the first anchor joint point. The included angle of the joint points changes in response to the user performing the to-be-detected movement.

In the second embodiment, the first anchor joint point is, for example, the ankle joint point 611, but the disclosure is not limited thereto. In addition, in response to determining that the to-be-detected movement is the squat, the processor 104 may use a hip joint point 614 and a knee joint point 615 of the user as the first joint point and the second joint point respectively, and use an included angle AN2 corresponding to the second joint point as the included angle AN of the joint points. Afterwards, in step S420, the processor 104 may determine the number of times the user performs the to-be-detected movement based on the change of the included angle AN of the joint points (e.g., the included angle AN2). For determining the number of times the user performs the squat for the to-be-detected movement, reference may be made to the determination of the number of times the user performs the push-up for the to-be-detected movement in the above embodiment. Thus, details in this regard will not be further reiterated in the following.

Taking FIG. 6 as an example, the upper limit value and the lower limit value of the reference value RV1 are, for example, 100% and 0%, respectively, and the processor 104 may present the value of the reference value RV1 in the images of the user in a form of a percentage bar 699. When the processor 104 determines that the user changes from the posture at the time point T1 (corresponding to the state where the reference value RV1 is 0%) to the posture at the time point T2 (corresponding to the state where the reference value RV1 is 100%) in FIG. 6, and then changes from the posture at the time point T2 to the posture at the time point T3 (corresponding to the state where the reference value RV1 is 0%), the processor 104 may determine that the reference value RV1 has met the above preset condition, and determine that the user has performed the squat once. On the other hand, if the reference value RV1 does not increase from 0% to 100%, or does not decrease from 100% to 0%, it means that the user has not completed a complete stroke of the squat. Therefore, the processor 104 may determine that the reference value RV1 does not meet the above preset condition, and thus the number of times the user performs the current set may not be accumulated.

After the user changes from the posture at the time point T4 to the posture at the time point T5, since the ankle joint points 611 and 612 have left the corresponding movable ranges R61 and R62, the processor 104 may determine that the user has stopped performing the current set of squats.

In some embodiments, the processor 104 may also perform the mechanism of FIG. 5 to recognize the correctness of the user performing the to-be-detected movement, which will be further described below with reference to FIG. 5.

In step S510, the processor 104 may find the reference joint points among the joint points of the user based on the to-be-detected movement. In step S520, the processor 104 may decide the connection line LN of the reference joint points based on the reference joint points. In step S520, the processor 104 may respectively use a shoulder joint point 616 and the ankle joint point 611 of the user as the reference joint points, and use the first connection line L1 between the shoulder joint point 616 and the ankle joint point 611 as the connection line LN of the reference joint points. In step S530, the processor 104 may determine the correctness of the user performing the to-be-detected movement based on the relative position between the first reference joint point RJ1 among the reference joint points and the connection line LN of the reference joint points.

In the scenario of FIG. 6, the processor 104 may use the shoulder joint point 616 of the user as the first reference joint point RJ1. Then, the current vertical distance VD between the first reference joint point RJ1 and the connection line LN of the reference joint points may be obtained, and the correctness of the user performing the to-be-detected movement may be estimated based on the current vertical distance VD and the length of the connection line LN of the reference joint points.

In some embodiments, the correctness of the user performing the to-be-detected movement is represented by the ratio of the current vertical distance VD to the length of the connection line LN of the reference joint points (e.g., VD/LN). In addition, in the case where the considered to-be-detected movement is the squat, the processor 104 may additionally use a ratio of the included angle AN2 of the knee joint point 615 to an included angle AN2' of the hip joint point 614 (e.g., AN2'/AN2) to estimate the correctness of the user performing the to-be-detected movement. Relevant principles of determining the correctness may be determined by a designer according to requirements.

For example, when the included angle AN2 of the knee joint point 615 is much less than the included angle AN2' of the hip joint point 614 (e.g., AN2/AN2' is greater than a certain threshold value), it means that the user performs the squat in a poor posture dominated by knees. In addition, when the included angle AN2 of the knee joint point 615 is much greater than the included angle AN2' of the hip joint point 614 (e.g., AN2/AN2' is less than the certain threshold value), and/or the vertical distance VD is too great (e.g., VD/LN is greater than the certain threshold value), it means that the user performs the squat in a poor posture with too much forward leaning. However, the disclosure is not limited thereto.

Figure 7:
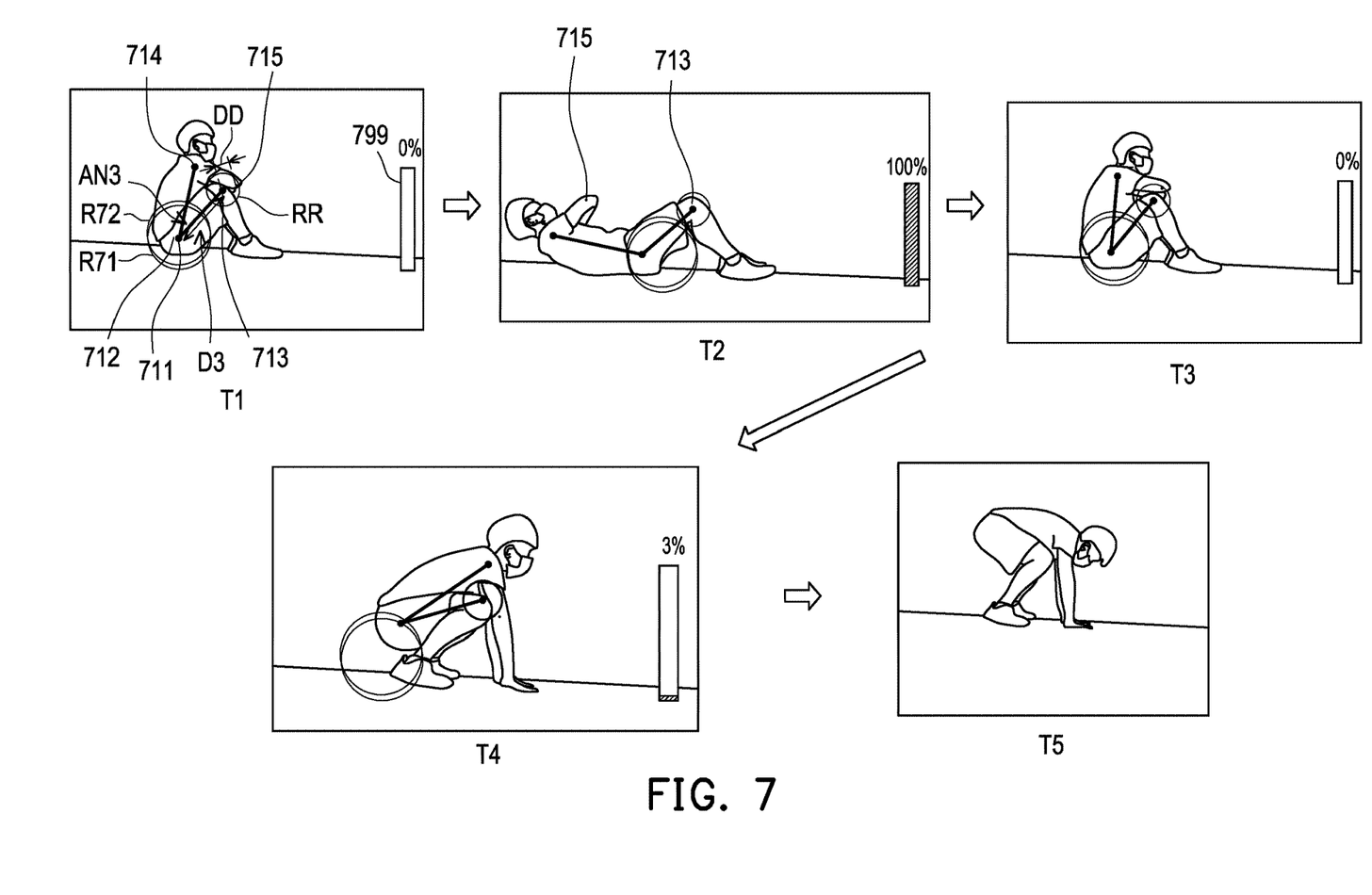
FIG. 7 is a schematic view of an application scenario according to the third embodiment of the disclosure.

Referring to FIG. 7, FIG. 7 is a schematic view of an application scenario according to the third embodiment of the disclosure. Five images of the user shown respectively correspond to the time points T1 to T5, for example. It is assumed that the to-be-detected movement determined in step S210 is the sit-up. Afterwards, the processor 104 may determine whether the user has presented an initial movement of the sit-up.

At the time point T1, since the posture of the user has been presented as the initial movement of the sit-up, the processor 104 may accordingly decide the anchor joint point among the joint points of the user, and may determine that hip joint points 711 and 712 (respectively corresponding to a right hip and a left hip of the user) of the user are the anchor joint points, and decide the movable ranges of the anchor joint points. In FIG. 7, the processor 104 may obtain a knee joint point 713 of the user, and decide the designated length R1 based on a third distance D3 between the hip joint point 711 and the corresponding knee joint point 713. The processor 104 may use half of the third distance D3 as the designated length R1, and define movable ranges R71 and R72 accordingly. The movable range R71 is, for example, a circular range with the hip joint point 711 as the center of circle and the designated length R1 as the radius, while the movable range R72 is, for example, a circular range with the hip joint point 712 as the center of circle and the designated length R1 as the radius. However, the disclosure is not limited thereto. After the movable ranges R71 and R72 are decided, positions of the movable ranges R71 and R72 in the image are fixed.

Afterwards, the processor 104 may determine whether the hip joint points 711 and 712 leave the corresponding movable ranges R71 and R72. If so, it means that the user has stopped performing the sit-up (e.g., the state at the time point T5). If not, it means that the user is still in a process of performing the sit-up.

In some embodiments, similarly, the processor 104 may also recognize the number of times the user performs the to-be-detected movement based on the mechanism of FIG. 4, which will be further described below with reference to FIG. 4.

In step S410, the processor 104 may decide the first joint point and the second joint point of the user according to the to-be-detected movement, and decide the included angle AN of the joint points according to the first joint point, the second joint point, and the first anchor joint point. The included angle of the joint points changes in response to the user performing the to-be-detected movement. The first anchor joint point is, for example, the hip joint point 711, but the disclosure is not limited thereto. In addition, the processor 104 may use a shoulder joint point 714 and the knee joint point 713 of the user as the first joint point and the second joint point respectively, and use an included angle AN3 corresponding to the first anchor joint point as the included angle AN of the joint points. Afterwards, in step S420, the processor 104 may determine the number of times the user performs the to-be-detected movement based on the change of the included angle AN of the joint points (e.g., the included angle AN3). For determining the number of times the user performs the squat for the to-be-detected movement, reference may be made to the determination of the number of times the user performs the push-up for the to-be-detected movement in the above embodiment. Thus, details in this regard will not be further reiterated in the following.

Taking FIG. 7 as an example, the upper limit value and the lower limit value of the reference value RV1 are, for example, 100% and 0%, respectively, and the processor 104 may present the value of the reference value RV1 in the images of the user in a form of a percentage bar 799. When the processor 104 determines that the user changes from the posture at the time point T1 (corresponding to the state where the reference value RV1 is 0%) to the posture at the time point T2 (corresponding to the state where the reference value RV1 is 100%) in FIG. 7, and then changes from the posture at the time point T2 to the posture at the time point T3 (corresponding to the state where the reference value RV1 is 0%), the processor 104 may determine that the reference value RV1 has met the above preset condition, and determine that the user has performed the sit-up once. On the other hand, if the reference value RV1 does not increase from 0% to 100%, or does not decrease from 100% to 0%, it means that the user has not completed a complete stroke of the sit-up. Therefore, the processor 104 may determine that the reference value RV1 does not meet the above preset condition, and thus the number of times the user performs the current set may not be accumulated.

In addition, after the user changes from the posture at the time point T4 to the posture at the time point T5, since the hip joint points 711 and 712 have left the corresponding movable ranges R71 and R72, the processor 104 may determine that the user has stopped performing the current set of sit-ups.

After the user changes from the posture at the time point T4 to the posture at the time point T5, since the hip joint points 711 and 712 have left the corresponding movable ranges R71 and R72, the processor 104 may determine that the user has stopped performing the current set of sit-ups.

In some embodiments, the processor 104 may further recognize the correctness of the user performing the to-be-detected movement based on the images of the user during the to-be-detected movement, which will be further described below with reference to FIG. 8.

Figure 8:
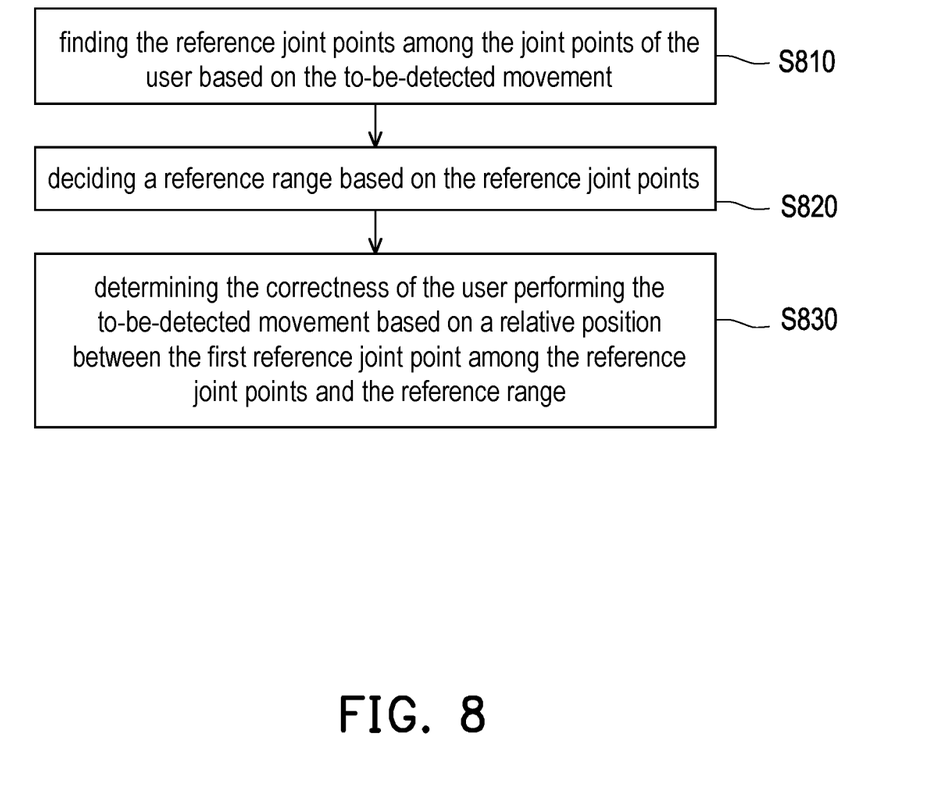
FIG. 8 is a flowchart of recognizing correctness of a movement according to the third embodiment of the disclosure.

Referring to FIG. 8, FIG. 8 is a flowchart of recognizing correctness of a movement according to the third embodiment of the disclosure. For ease of description, the scenario shown in FIG. 7 is taken as an example for description below. In step S810, the processor 104 may find the reference joint points among the joint points of the user based on the to-be-detected movement. In step S820, the processor 104 may decide a reference range RN based on the reference joint points. The processor 104 may respectively use an elbow joint point 715 and the knee joint point 713 of the user as the reference joint points, and determine a reference radius based on a distance DD between the elbow joint point 715 and the knee joint point 713. Afterwards, a reference range RR is decided based on the knee joint point 713 and the reference radius. The reference range RR is, for example, a circular region with the knee joint point 713 as the center of circle and the reference radius (i.e., the distance DD) as the radius, but the disclosure is not limited thereto.

Then, in step S830, the processor 104 may use the elbow joint point 715 of the user as the first reference joint point RJ1. Afterwards, the processor 104 may determine whether the elbow joint point 715 has entered the reference range RR in a process of the user performing the sit-up once. In response to determining that the elbow joint point 715 has entered the reference range RR in the process of the user performing the sit-up once, it means that the user has completely performed a stroke of the sit-up. Therefore, the processor 104 may accordingly determine that the user has performed the sit-up correctly. On the other hand, in response to determining that the elbow joint point 715 has not entered the reference range RR in the process of the user performing the sit-up once, it means that the user has only completed the partial stroke of the sit-up. Therefore, the processor 104 may determine that the user does not perform the sit-up correctly.

Figure 9:
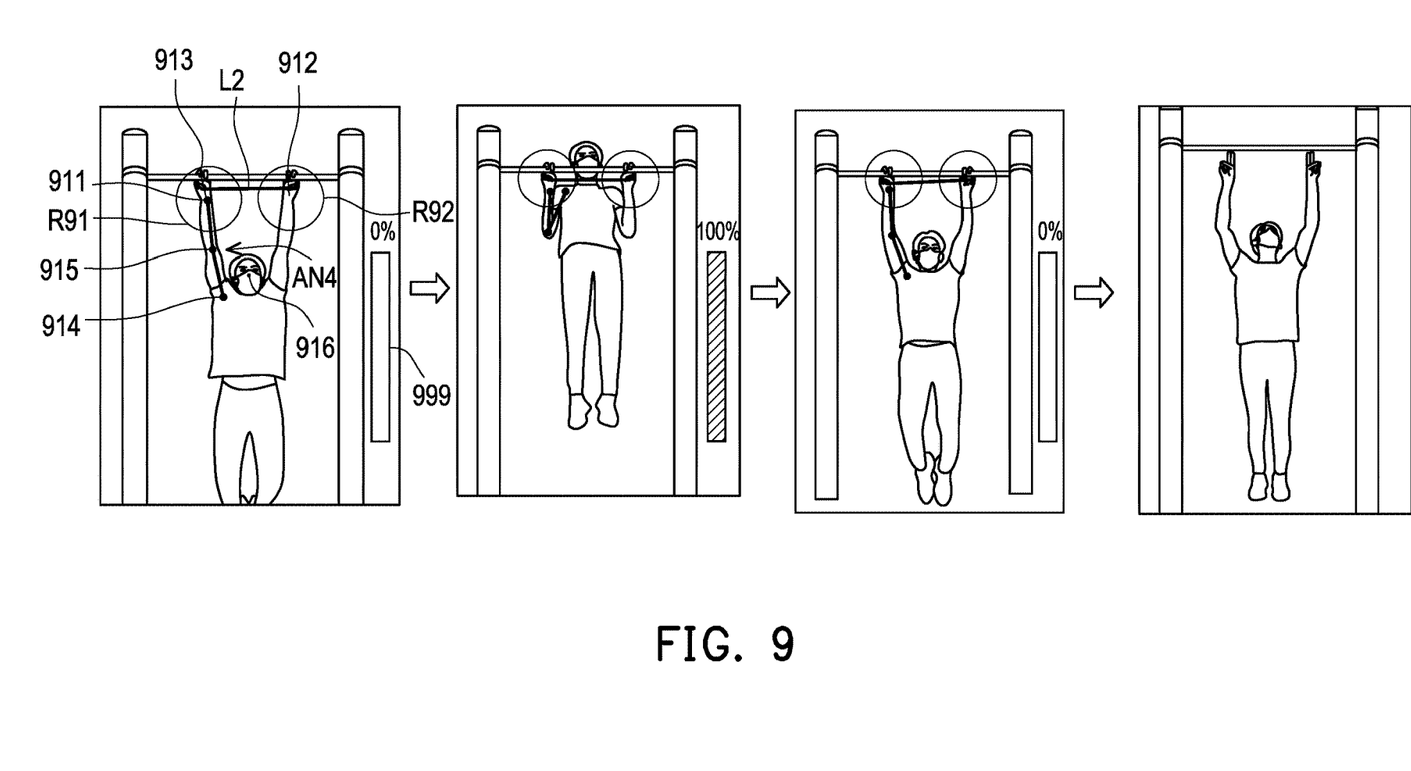
FIG. 9 is a schematic view of an application scenario according to the fourth embodiment of the disclosure.

Referring to FIG. 9, FIG. 9 is a schematic view of an application scenario according to the fourth embodiment of the disclosure. In FIG. 9, five images of the user shown respectively correspond to the time points T1 to T5, for example. In the fourth embodiment, it is assumed that the to-be-detected movement determined in step S210 is the pull-up. Afterwards, the processor 104 may determine whether the user has presented an initial movement of the pull-up.

At the time point T1, since the posture of the user has been presented as the initial movement of the pull-up (e.g., a posture of raising both hands upward), the processor 104 may accordingly decide the anchor joint point among the joint points of the user, and may determine that wrist joint points 911 and 912 (respectively corresponding to a right wrist and a left wrist of the user) of the user are the anchor joint points and decide the movable ranges of the anchor joint points. In FIG. 9, the processor 104 may obtain a finger joint point 913 of the user, and decide the designated length R1 based on the second distance D2 between the wrist joint point 911 and the corresponding finger joint point 913. The processor 104 may directly use the third distance D3 as the designated length R1, and define movable ranges R91 and R92 accordingly. The movable range R91 is, for example, a circular range with the wrist joint point 911 as the center of circle and the designated length R1 as the radius, while the movable range R92 is, for example, a circular range with the wrist joint point 912 as the center of circle and the designated length R1 as the radius. However, the disclosure is not limited thereto. After the movable ranges R91 and R92 are decided, positions of the movable ranges R91 and R92 in the image are fixed.

Afterwards, the processor 104 may determine whether the wrist joint points 911 and 912 leave the corresponding movable ranges R91 and R92. If so, it means that the user has stopped performing the pull-up (e.g., the state at the time point T5). If not, it means that the user is still in a process of performing the pull-up.

In some embodiments, similarly, the processor 104 may also recognize the number of times the user performs the to-be-detected movement based on the mechanism of FIG. 4, which will be further described below.

In step S410, the processor 104 may decide the first joint point and the second joint point of the user according to the to-be-detected movement, and decide the included angle AN of the joint points according to the first joint point, the second joint point, and the first anchor joint point. The included angle of the joint points changes in response to the user performing the to-be-detected movement. The first anchor joint point is, for example, the wrist joint point 911, but the disclosure is not limited thereto. In addition, the processor 104 may use a shoulder joint point 914 and an elbow joint point 915 of the user as the first joint point and the second joint point respectively, and use an included angle AN4 corresponding to the second joint point as the included angle AN of the joint points. Afterwards, in step S420, the processor 104 may determine the number of times the user performs the to-be-detected movement based on the change of the included angle AN of the joint points (e.g., the included angle AN4). For determining the number of times the user performs the squat for the to-be-detected movement, reference may be made to the determination of the number of times the user performs the push-up for the to-be-detected movement in the above embodiment. Thus, details in this regard will not be further reiterated in the following.

Taking FIG. 9 as an example, the upper limit value and the lower limit value of the reference value RV1 are, for example, 100% and 0%, respectively, and the processor 104 may present the value of the reference value RV1 in the images of the user in a form of a percentage bar 999. When the processor 104 determines that the user changes from the posture at the time point T1 (corresponding to the state where the reference value RV1 is 0%) to the posture at the time point T2 (corresponding to the state where the reference value RV1 is 100%) in FIG. 9, and then changes from the posture at the time point T2 to the posture at the time point T3 (corresponding to the state where the reference value RV1 is 0%), the processor 104 may determine that the reference value RV1 has met the above preset condition, and determine that the user has performed the pull-up once. On the other hand, if the reference value RV1 does not increase from 0% to 100%, or does not decrease from 100% to 0%, it means that the user has not completed a complete stroke of the pull-up. Therefore, the processor 104 may determine that the reference value RV1 does not meet the above preset condition, and thus the number of times the user performs the current set may not be accumulated.

After the user changes from the posture at the time point T4 to the posture at the time point T5, since the wrist joint points 911 and 912 have left the corresponding movable ranges R91 and R92, the processor 104 may determine that the user has stopped performing the current set of pull-ups.

In some embodiments, the processor 104 may also perform the mechanism of FIG. 5 to recognize the correctness of the user performing the to-be-detected movement, which will be further described below with reference to FIG. 5.

In step S510, the processor 104 may find the reference joint points among the joint points of the user based on the to-be-detected movement. In step S520, the processor 104 may decide the connection line LN of the reference joint points based on the reference joint points.

In the fourth embodiment, in response to determining that the to-be-detected movement is the pull-up, the processor 104 may respectively use the wrist joint points 911 and 912 and a nose joint point 916 of the user as the reference joint points, and use a second connection line L2 between the wrist joint points 911 and 912 as the connection line LN of the reference joint points. Then, in step S530, the processor 104 may determine the correctness of the user performing the to-be-detected movement based on the relative position between the first reference joint point RJ1 among the reference joint points and the connection line LN of the reference joint points.

In the scenario of FIG. 9, the processor 104 may use the nose joint point 916 of the user as the first reference joint point RJ1. Afterwards, the processor 104 may determine whether a height of the nose joint point 916 has exceeded a height of the connection line LN of the reference joint points in a process of the user performing the pull-up once. If so, it means that the user has completely performed a stroke of the pull-up. Therefore, the processor 104 may determine that the user has performed the pull-up correctly. On the other hand, if the height of the nose joint point 916 does not exceed the height of the connection line LN of the reference joint points in the process of the user performing the pull-up once, it means that the user has not completely performed the stroke of the pull-up. Therefore, the processor 104 may determine that the user has not performed the pull-up correctly.

In an embodiment, in response to determining that the user has stopped performing the to-be-detected movement, the processor 104 may accordingly determine that the user has completed a set of to-be-detected movements. The set of to-be-detected movements may include at least one to-be-detected movement. Afterwards, the processor 104 may estimate motion data of each of the to-be-detected movements performed by the user.

In some embodiments, the above motion data includes, for example, calorie consumption and a movement speed, etc. The estimation of the calorie consumption may refer to the content of the document, "Corrected METs", while the estimation of the movement speed may refer to the content of Taiwan Patent Application No. 110148854 (the content of which is incorporated herein by reference). However, the disclosure is not limited thereto.

The disclosure further provides a computer-readable storage medium for performing the movement determination method. The computer-readable storage medium is formed by multiple program instructions (e.g., the program instructions of setup and deployment). The program instructions may be loaded into the movement determination device 100 for execution to perform the movement determination method and functions of the movement determination device 100.

Based on the above, in the embodiment of the disclosure, in addition to determining whether the user has stopped performing the to-be-detected movement based on the relative position of the anchor joint point and the movable range, the number of times the user performs the current set of to-be-detected movements may also be determined based on the change of the included angle between the considered joint points, and the correctness of the user performing the to-be-detected movement is determined based on the relative position between the first reference joint point and the reference range/connection line of the reference joint points.

As a result, the disclosure provides the novel and intelligent movement determination method, which may correctly and effectively determine the process of the user performing the to-be-detected movement, and calculate the times of performance, number of sets, speed, energy consumption, and other related values of the to-be-detected movement.

Although the disclosure has been described with reference to the above embodiments, they are not intended to limit the disclosure. It will be apparent to one of ordinary skill in the art that modifications to the described embodiments may be made without departing from the spirit and the scope of the disclosure. Accordingly, the scope of the disclosure will be defined by the attached claims and their equivalents and not by the above detailed descriptions.

What is claimed is:

1. A movement determination method, suitable for a movement determination device, comprising:
    obtaining a plurality of images of a user, and feeding the images of the user into a machine learning model, wherein the machine learning model determines whether the user has presented an initial movement corresponding to a to-be-detected movement according to the images of the user;
    in response to determining that the user has presented the initial movement corresponding to the to-be-detected movement, deciding at least one anchor joint point among a plurality of joint points of the user based on the to-be-detected movement;
    deciding a movable range of each of the anchor joint points; and
    in response to determining that each of the anchor joint points leaves the corresponding movable range, determining that the user has stopped performing the to-be-detected movement.

2. The method according to claim 1, wherein deciding the at least one anchor joint point among the joint points of the user based on the to-be-detected movement comprises:
    in response to determining that the to-be-detected movement is a push-up or a pull-up, detecting at least one wrist joint point of the user as the at least one anchor joint point;
    in response to determining that the to-be-detected movement is a squat, detecting at least one ankle joint point of the user as the at least one anchor joint point; and
    in response to determining that the to-be-detected movement is a sit-up, detecting at least one hip joint point of the user as the at least one anchor joint point.

3. The method according to claim 1, wherein deciding the movable range of each of the anchor joint points comprises:
  deciding a designated length; and
  deciding a geometric region as the movable range of each of the anchor joint points based on each of the anchor joint points and the designated length.

4. The method according to claim 3, wherein deciding the designated length comprises:
  in response to determining that the at least one anchor joint point is at least one wrist joint point of the user, obtaining at least one finger joint point of the user, and deciding the designated length based on a first distance between the at least one wrist joint point and the corresponding at least one finger joint point;
  in response to determining that the at least one anchor joint point is at least one ankle joint point of the user, obtaining at least one toe joint point of the user, and deciding the designated length based on a second distance between the at least one ankle joint point and the corresponding at least one toe joint point; and
  in response to determining that the at least one anchor joint point is at least one hip joint point of the user, obtaining at least one knee joint point of the user, and deciding the designated length based on a third distance between the at least one hip joint point and the corresponding at least one knee joint point.

5. The method according to claim 1, wherein the at least one anchor joint point comprises a first anchor joint point, and after deciding the movable range of each of the anchor joint points, the method further comprises:
  deciding a first joint point and a second joint point of the user according to the to-be-detected movement, and deciding an included angle of the joint points according to the first joint point, the second joint point, and the first anchor joint point, wherein the included angle of the joint points changes in response to the user performing the to-be-detected movement; and
  determining a number of times the user performs the to-be-detected movement based on a change of the included angle of the joint points.

6. The method according to claim 5, wherein determining the number of times the user performs the to-be-detected movement based on the change of the included angle of the joint points comprises:
  deciding a current angle change amount based on a current angle value and an initial angle value of the included angle of the joint points;
  deciding a reference value based on the current angle change amount of the included angle of the joint points, an angle upper limit value of the joint points, and an angle lower limit value of the joint points; and
  in response to determining that a change of the reference value meets a preset condition, determining that the user has performed the to-be-detected movement once.

7. The method according to claim 6, wherein in response to determining that the reference value has changed from a lower limit value to an upper limit value, and then from the upper limit value back to the lower limit value, it is determined that the reference value has met the preset condition.

8. The method according to claim 5, wherein deciding the first joint point and the second joint point of the user according to the to-be-detected movement, and deciding the included angle of the joint points according to the first joint point, the second joint point, and the first anchor joint point comprises:
  in response to determining that the to-be-detected movement is a push-up, using a shoulder joint point and a toe joint point of the user as the first joint point and the second joint point respectively, and using an included angle corresponding to the second joint point as the included angle of the joint points;
  in response to determining that the to-be-detected movement is a squat, using a hip joint point and a knee joint point of the user as the first joint point and the second joint point respectively, and using the included angle corresponding to the second joint point as the included angle of the joint points;
  in response to determining that the to-be-detected movement is a sit-up, using the shoulder joint point and the knee joint point of the user as the first joint point and the second joint point respectively, and using an included angle corresponding to the first anchor joint point as the included angle of the joint points; and
  in response to determining that the to-be-detected movement is a pull-up, using the shoulder joint point and an elbow joint point as the first joint point and the second joint point respectively, and using the included angle corresponding to the second joint point as the included angle of the joint points.

9. The method according to claim 1, wherein after deciding the movable range of each of the anchor joint points, the method further comprises:
  finding a plurality of reference joint points among the joint points of the user based on the to-be-detected movement;
  deciding a connection line of the reference joint points based on the reference joint points; and
  determining correctness of the user performing the to-be-detected movement based on a relative position between a first reference joint point among the reference joint points and the connection line of the reference joint points.

10. The method according to claim 9, wherein
  in response to determining that the to-be-detected movement is a push-up, using a shoulder joint point, an ankle joint point, and a hip joint point of the user as the reference joint points respectively, and using a first connection line between the shoulder joint point and the ankle joint point as the connection line of the reference joint points;
  in response to determining that the to-be-detected movement is a squat, using the shoulder joint point and the ankle joint point of the user as the reference joint points respectively, and using the first connection line between the shoulder joint point and the ankle joint point as the connection line of the reference joint points; and
  in response to determining that the to-be-detected movement is a pull-up, using a plurality of wrist joint points and a nose joint of the user as the reference joint points respectively, and using a second connection line between the wrist joint points as the connection line of the reference joint points.

11. The method according to claim 9, wherein determining the correctness of the user performing the to-be-detected movement based on the relative position between the first reference joint point among the reference joint points and the connection line of the reference joint points comprises:
  in response to determining that the to-be-detected movement is a push-up, using a hip joint point of the user as the first reference joint point;

in response to determining that the to-be-detected movement is a squat, using a shoulder joint of the user as the first reference joint;

obtaining a current vertical distance between the first reference joint point and the connection line of the reference joint points; and estimating the correctness of the user performing the to-be-detected movement based on the current vertical distance and a length of the connection line of the reference joint points.

12. The method according to claim 11, wherein the correctness of the user performing the to-be-detected movement is represented by a ratio of the current vertical distance to the length of the connection line of the reference joint points.

13. The method according to claim 9, wherein determining the correctness of the user performing the to-be-detected movement based on the relative position between the first reference joint point among the reference joint points and the connection line of the reference joint points comprises:

in response to determining that the to-be-detected movement is a pull-up, using a nose joint point of the user as the first reference joint;

in response to determining that a height of the nose joint point has exceeded a height of the connection line of the reference joint points in a process of the user performing the pull-up once, determining that the user has performed the pull-up correctly; and in response to determining that the height of the nose joint point has not exceeded the height of the connection line of the reference joint points in the process of the user performing the pull-up once, determining that the user has not performed the pull-up correctly.

14. The method according to claim 1, wherein after deciding the movable range of each of the anchor joint points, the method further comprises:

finding a plurality of reference joint points among the joint points of the user based on the to-be-detected movement;

deciding a reference range based on the reference joint points; and determining correctness of the user performing the to-be-detected movement based on a relative position between a first reference joint point among the reference joint points and the reference range.

15. The method according to claim 14, comprising:

in response to determining that the to-be-detected movement is a sit-up, using an elbow joint point and a knee joint point of the user as the reference joint points, and deciding a reference radius based on a distance between the elbow joint point and the knee joint point; and deciding the reference range based on the knee joint point and the reference radius.

16. The method according to claim 14, wherein determining the correctness of the user performing the to-be-detected movement based on the relative position between the first reference joint point among the reference joint points and the reference range comprises:

in response to determining that the to-be-detected movement is a sit-up, using an elbow joint point of the user as the first reference joint point;

in response to determining that the elbow joint point has entered the reference range in a process of the user performing the sit-up once, determining that the user has performed the sit-up correctly; and in response to determining that the elbow joint point has not entered the reference range in the process of the user performing the sit-up once, determining that the user has not performed the sit-up correctly.

17. The method according to claim 1, further comprising:

in response to determining that the user has stopped performing the to-be-detected movement, determining that the user has completed a set of the to-be-detected movements; and estimating at least one motion data of the to-be-detected movement each time the user performs.

18. A movement determination device, comprising:

a non-transitory storage circuit storing a program code; and a processor coupled to the non-transitory storage circuit and accessing the program code to perform:

obtaining a plurality of images of a user, and feeding the images of the user into a machine learning model, wherein the machine learning model determines whether the user has presented an initial movement corresponding to a to-be-detected movement according to the images of the user;

in response to determining that the user has presented the initial movement corresponding to the to-be-detected movement, deciding at least one anchor joint point among a plurality of joint points of the user based on the to-be-detected movement;

deciding a movable range of each of the anchor joint points; and in response to determining that each of the anchor joint points leaves the corresponding movable range, determining that the user has stopped performing the to-be-detected movement.

19. A non-transitory computer-readable storage medium, wherein the computer-readable storage medium records an executable computer program, and the executable computer program is loaded by a movement determination device to perform:

obtaining a plurality of images of a user, and feeding the images of the user into a machine learning model, wherein the machine learning model determines whether the user has presented an initial movement corresponding to a to-be-detected movement according to the images of the user;

in response to determining that the user has presented the initial movement corresponding to the to-be-detected movement, deciding at least one anchor joint point among a plurality of joint points of the user based on the to-be-detected movement;

deciding a movable range of each of the anchor joint points; and in response to determining that each of the anchor joint points leaves the corresponding movable range, determining that the user has stopped performing the to-be-detected movement.

* * * * *